United States Patent
Ahmed et al.

(10) Patent No.: US 12,083,220 B1
(45) Date of Patent: Sep. 10, 2024

(54) COMBINATION TREATMENT FOR ANTIBIOTIC RESISTANT INFECTIONS

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Mohamed Ahmed El-Mokhtar, Al-Ahsa (SA); Mohammed Sherif Saddik Ibrahim, Al-Ahsa (SA); Ahmed Mohammed Abu-Dief Mohammed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/512,722

(22) Filed: Nov. 17, 2023

Related U.S. Application Data

(62) Division of application No. 18/192,432, filed on Mar. 29, 2023.

(51) Int. Cl.
| | | |
|---|---|---|
| *A61K 9/06* | (2006.01) | |
| *A61K 31/5377* | (2006.01) | |
| *A61K 31/546* | (2006.01) | |
| *A61K 47/38* | (2006.01) | |
| *A61K 47/69* | (2017.01) | |
| *A61P 17/02* | (2006.01) | |
| *A61P 31/04* | (2006.01) | |
| *B82Y 5/00* | (2011.01) | |

(52) U.S. Cl.
CPC ............ *A61K 9/06* (2013.01); *A61K 31/5377* (2013.01); *A61K 31/546* (2013.01); *A61K 47/38* (2013.01); *A61K 47/6903* (2017.08); *A61P 17/02* (2018.01); *A61P 31/04* (2018.01); *B82Y 5/00* (2013.01)

(58) Field of Classification Search
CPC .............. A61K 9/5115; A61K 2300/00; A61K 49/0093; A61K 33/30; A61K 31/5377; A61K 31/546; A61P 31/04
See application file for complete search history.

(56) References Cited

FOREIGN PATENT DOCUMENTS

| EP | 3300736 A1 | 4/2018 |
|---|---|---|
| WO | 2014/191109 A1 | 12/2014 |
| WO | 2017/124080 A1 | 7/2017 |

OTHER PUBLICATIONS

Habeeb et al (Pharmacia, Sep. 2022, vol. 69, pp. 855-864) (Year: 2022).*
Faella et al (Clinical Microbiology and Infection, 2006, vol. 12, pp. 391-394) (Year: 2006).*
Faella et al., "Combined treatment with ceftriaxone and linezolid of pneumococcal meningitis: a case series including penicillin-resistant strains," Clinical Microbiology and Infection, 2006.
Quanyun et al., "Compatibility and Stability of Linezolid Injection Admixed with Three Quinolone Antibiotics," Annals of Pharmacotherapy, 2000.

* cited by examiner

*Primary Examiner* — Mark V Stevens
(74) *Attorney, Agent, or Firm* — Nath, Goldberg & Meyer; Joshua B. Goldberg

(57) ABSTRACT

A combination treatment for antibiotic resistant infections is provided. The combination treatment for antibiotic resistant infections includes zinc oxide nanoparticles loaded with linezolid and ceftriaxone. The combination treatment may be formulated for administration by any desired route, including particularly oral administration or topical administration. The combination treatment may be administered to a subject in need thereof to treat a bacterial infection. The bacterial infection may be caused by any bacterium, including an antibiotic resistant bacterium. The combination treatment may be formulated in a gel for topical administration to improve wound healing and to treat a MRSA infection.

3 Claims, 1 Drawing Sheet

Specification includes a Sequence Listing.

COMBINATION TREATMENT FOR ANTIBIOTIC RESISTANT INFECTIONS

CROSS-REFERENCE TO RELATED APPLICATION

This application is a divisional of U.S. patent application Ser. No. 18/192,432, filed on Mar. 29, 2023, the entire contents of which are incorporated herein by reference.

SEQUENCE LISTING

The instant application contains a Sequence Listing which has been submitted in XML format via Patent Center and is hereby incorporated by reference in its entirety. Said XML copy, created on Jul. 19, 2023, is named 33101_35U_SE-Q_LISTING.xml and is 4,317 bytes in size.

BACKGROUND

1. Field

The disclosure of the present patent application relates to combination treatments for antibiotic resistant infections, and particularly to zinc oxide nanoparticles loaded with linezolid and ceftriaxone.

2. Description of the Related Art

Antimicrobial resistance is an ever-growing threat to human health. Resistance happens when germs like bacteria and fungi develop the ability to defeat the drugs designed to kill them. Resistant infections can be difficult, and sometimes impossible, to treat.

According to the CDC, antimicrobial resistance is an urgent global public health threat, killing at least 1.27 million people worldwide and associated with nearly 5 million deaths in 2019. In the U.S., more than 2.8 million antimicrobial-resistant infections occur each year. More than 35,000 people die as a result.

Antimicrobial resistance has the potential to affect people at any stage of life, as well as the healthcare, veterinary, and agriculture industries. This makes it one of the world's most urgent public health problems.

Bacteria and fungi do not have to be resistant to every antibiotic or antifungal to be dangerous. Resistance to even one antibiotic can cause serious problems. Antimicrobial-resistant infections that require the use of second- and third-line treatments can harm patients by causing serious side effects, such as organ failure, and prolong care and recovery, sometimes for months. Many medical advances are dependent on the ability to fight infections using antibiotics, including joint replacements, organ transplants, cancer therapy, and the treatment of chronic diseases like diabetes, asthma, and rheumatoid arthritis. In some cases, the development of new antimicrobial resistance may result in infections that have no treatment options.

While new antibiotics have been a focus of much work in recent years, the growth of antibiotic resistance continues to outpace the development of new treatments, and many promising antibiotics have been found to result in problematic side effects.

Thus, a combination treatment for antibiotic resistance infections solving the aforementioned problems is desired.

SUMMARY

The combination treatment for antibiotic resistant infections includes zinc oxide nanoparticles loaded with linezolid and ceftriaxone. The combination treatment may be formulated for administration by any desired route, including oral administration or topical administration. The combination treatment may be administered to a subject in need thereof to treat a bacterial infection. The bacterial infection may be caused by any bacterium, and in particular embodiments may be caused by an antibiotic resistant bacterium. In a particular embodiment the combination treatment may be formulated in a gel for topical administration to improve wound healing and to treat a MRSA infection.

An embodiment of the present subject matter is directed to a pharmaceutical composition including the zinc oxide nanoparticles loaded with linezolid and ceftriaxone and a pharmaceutically acceptable carrier.

An embodiment of the present subject matter is directed to a method of making a pharmaceutical composition including mixing the zinc oxide nanoparticles loaded with linezolid and ceftriaxone under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of treating a bacterial infection, including administering to a subject in need thereof a therapeutically effective amount of a pharmaceutical composition according to the present subject matter.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
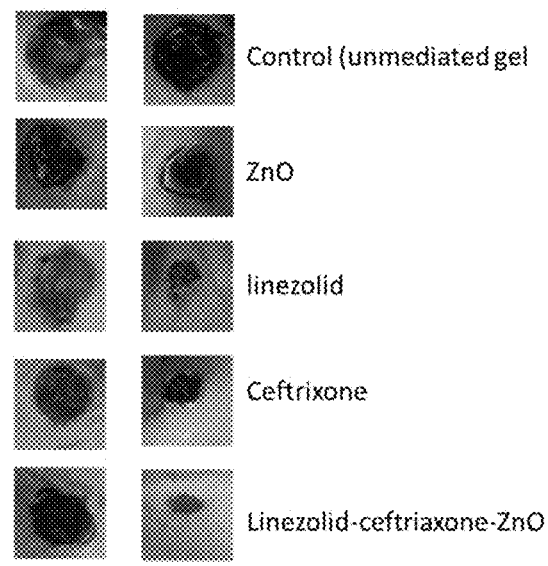
FIG. 1A depicts day 1 and day 5 post-infection photographs of wounds of rats inoculated with MRSA and treated with either an unmedicated gel, a gel loaded with ZnO nanoparticles, a gel loaded with linezolid, a gel loaded with ceftriaxone, or a gel loaded with linezolid-ceftriaxone-ZnO nanoparticles.

The following definitions are provided for the purpose of understanding the present subject matter and for construing the appended patent claims.

Definitions

As used herein, "MRSA" refers to methicillin-resistant *Staphylococcus aureus*, an infection caused by a type of staph bacteria that has become resistant to many of the antibiotics traditionally used to treat ordinary (i.e. non-resistant) staph infections.

As used herein, "Ceftriaxone" refers to a cephalosporin antibiotic having the chemical formula $C_{18}H_{18}N_8O_7S_3$ and registered under CAS Number 73384-59-5.

As used herein, "Linezolid" refers to a protein synthesis inhibiting antibiotic having the chemical formula $C_{16}H_{20}FN_3O_4$ and registered under CAS Number 165800-03-3.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The combination treatment for antibiotic resistant infections includes zinc oxide nanoparticles loaded with linezolid and ceftriaxone. The combination treatment may be formulated for administration by any desired route, including particularly oral administration or topical administration. The combination treatment may be administered to a subject in need thereof to treat a bacterial infection. The bacterial infection may be caused by any bacterium, and in particular embodiments may be caused by an antibiotic resistant bacterium. In a particular embodiment the combination treatment may be formulated in a gel for topical administration to improve wound healing and to treat a MRSA infection.

An embodiment of the present subject matter is directed to a pharmaceutical composition comprising the zinc oxide nanoparticles loaded with linezolid and ceftriaxone and a pharmaceutically acceptable carrier.

An embodiment of the present subject matter is directed to a method of making a pharmaceutical composition including mixing the zinc oxide nanoparticles loaded with linezolid and ceftriaxone with a pharmaceutically acceptable carrier. For example, the method of making a pharmaceutical composition can include mixing the zinc oxide nanoparticles loaded with linezolid and ceftriaxone under sterile conditions with a pharmaceutically acceptable carrier with preservatives, buffers, and/or propellants to create the pharmaceutical composition.

An embodiment of the present subject matter is directed to a pharmaceutical composition including the zinc oxide nanoparticles loaded with linezolid and ceftriaxone. To prepare the pharmaceutical composition, the zinc oxide nanoparticles loaded with linezolid and ceftriaxone, as an active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral, parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the zinc oxide nanoparticles loaded with linezolid and ceftriaxone or an amount effective to treat a disease, such as a disease associated with a bacterial infection, may be determined initially from the Examples described herein and adjusted for specific targeted diseases using routine methods.

The zinc oxide nanoparticles loaded with linezolid and ceftriaxone can be administered to a subject in need thereof. For example, the antioxidant probiotic nanoparticles can be used to treat a subject suffering from a disease associated with a bacterial infection. The disease can be infection with MRSA or other diseases associated with antibiotic resistant bacterial infections.

An embodiment of the present subject matter is directed to a method of treating a bacterial infection, comprising administering to a subject in need thereof a therapeutically effective amount of the pharmaceutical composition according to the present subject matter.

The zinc oxide nanoparticles loaded with linezolid and ceftriaxone, or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The present compositions may be used to treat bacterial infections, including particular antibiotic resistant bacterial infections. Antibiotic resistant bacterial infections may be caused by a wide range of bacteria, including commonly *Escherichia coli*, *Staphylococcus aureus*, *Klebsiella pneumoniae*, *Streptococcus pneumoniae*, *Acinetobacter baumannii*, *Pseudomonas aeruginosa*, and *Neisseria gonorrhoeae*. It is anticipated that the present compositions may be effective to treat further antibiotic resistant bacteria that may come to prominence in the future, whether due to increased spread of a known antibiotic resistant bacteria or the development or discovery of one or more new antibiotic resistant bacteria. In a particular embodiment of interest, the antibiotic resistant bacteria may be *Staphylococcus aureus* and in certain embodiments the antibiotic resistant *Staphylococcus aureus* may be MRSA.

The zinc oxide nanoparticles (ZnONPs) may be any ZnONPs produced by any method known in the art. By way of example, the ZnONPs may be produced by chemical, physical, or green synthesis routes well-known in the art, including but not limited to laser ablation, hydrothermal methods, electrochemical depositions, sol-gel method, chemical vapor deposition, thermal decomposition, combustion methods, ultrasound, microwave-assisted combustion method, two-step mechanochemical-thermal synthesis, anodization, co-precipitation, electrophoretic deposition, and precipitation processes.

In some embodiments the ZnONPs may be green ZnONPs produced by mixing a source of zinc with a plant extract. In further embodiments the source of zinc may be zinc nitrate hexahydrate, the plant extract may be a liquid extract of *Echinacea purpurea*, and the nanoparticles may be produced by heating the liquid extract of *Echinacea purpurea*, adding the zinc nitrate hexahydrate, and allowing a precipitate of ZnONPs to form. The precipitate may then optionally be dried in an oven and further heated to 400° C. for two hours.

In the compositions disclosed herein, the ZnONPs may be loaded with both Ceftriaxone and Linezolid. The drug loading of the nanoparticles may be accomplished by any technique known in the art, including adsorption or surface functionalization using ligands, linker chains, drugs, and markers.

In some embodiments, the ZnONPs may be loaded with both Ceftriaxone and Linezolid by mixing an aqueous solution of ZnONPs with aqueous solutions of Ceftriaxone and Linezolid and shaking the resulting mixture for a period of time at room temperature. In some embodiments, the shaking may be achieved by a water bath shaker for a period of 9, 10, 11, 12, 13, 14, or 15 hours.

Where topical applications are desired, such as for wound healing or for treatment of a topical bacterial infection, the Ceftriaxone/Linezolid loaded ZnONPs may be impregnated into a gel. The gel may be any gel known to be useful for topical applications. By way of non-limiting example, the gel may be a hydrogel, a MAP gel (microporous annealed particle gel), a swellable polymer gel, a collagen based gel, or the like. The gel formulation may assist in achieving extended contact between the Ceftriaxone/Linezolid loaded ZnONPs and the wound site.

In some embodiments the Ceftriaxone/Linezolid loaded ZnONPs may be impregnated in a HPMC gel. These gels may be prepared at a HPMC concentration of between 2.0%-3.0%. For example, the gels may be prepared at a HPMC concentration of 2.0%, 2.1%, 2.2%, 2.3%, 2.4%, 2.5%, 2.6%, 2.7%, 2.8%, 2.9%, or 3.0%. The gels may be prepared by dispersing HPMC in preheated water and stirring to obtain a homogenous mixture. Linezolid-ceftriaxone loaded-ZnO nanoparticles may then be added. In certain embodiments, the Linezolid-ceftriaxone loaded-ZnO nanoparticles may be added at a concentration between 0.5% and 1.5% (w/w), including at concentrations of 0.5%, 0.6%, 0.7%, 0.8%, 0.9%, 1.0%, 1.1%, 1.2%, 1.3%, 1.4%, or 1.5% (w/w). The stirring may be maintained until a homogenous distribution is achieved and the gel may then optionally be cast in any suitable mold.

The combination treatment for antibiotic resistant infections may be better understood in view of the following examples.

Example 1

Green Synthesis of Zinc Oxide Nanoparticles

Zinc oxide nanoparticles were prepared using zinc nitrate hexahydrate ($Zn(NO_3)_2 \cdot 6H_2O$) solution and *Echinacea purpurea* liquid extract (a reducing and capping agent).

*Echinacea purpurea* liquid extract (about 100 mL) was heated at (80° C.) on a magnetic stirrer. When the temperature of the extract reached 80° C., 5 g of zinc nitrate hexahydrate ($Zn(NO_3)_2 \cdot 6H_2O$) was added and left for about 2 h till a white precipitate appeared. The precipitate was then dried in an oven at 60° C. for 12 hr. Afterwards, the resulting creamy paste was collected to a ceramic crucible cup and heated in muffle at 400° C. for 2 h. The resultant zinc oxide nanoparticles (in the form of a white powder) were stored in an airtight container for further use.

Example 2

Preparation of Ceftriaxone/Linezolid-Loaded Zinc Oxide Nanoparticles

In a flask, an aqueous solution of the prepared zinc oxide NPs (250 ml solvent:100 mg nanoparticles) was added to a previously prepared aqueous solution (200 mL solvent) containing 50 mg of ceftriaxone sodium and 50 mg of linezolid. The flask was placed in a thermostatically controlled water bath shaker operated at 500 rpm for 12 h at room temperature (25° C.). Finally, the resulting ceftriaxone/linezolid-loaded Zinc oxide NPs were separated from the solution by filtration using a membrane filter with 0.22 µm pore size (Millipore Filters, MA, USA). The unbound ceftriaxone and linezolid concentration was determined in the filtrate using HPLC.

Example 3

Preparation of Linezolid, Ceftriaxone Sodium, Plain ZnONPs, and Linezolid-Ceftriaxone Loaded ZnONP Impregnated HPMC Gels Hydroxypropyl methylcellulose (HPMC) was used as a gelling agent at a concentration level of 2.5% (w/v). Gels were prepared by dispersing the HPMC polymer in pre-heated distilled water (80° C.). Then the prepared dispersion was stirred at 1000 rpm using a magnetic stirrer (Thermo Fisher Scientific, NJ, USA) until a homogenous mixture was attained. Individual gels were then prepared by adding different medications to the prepared gel base, including linezolid (0.129% w/w), ceftriaxone sodium (0.112% w/w), Linezolid-ceftriaxone loaded-ZnO nanoparticles prepared according to Example 2 (1% w/w containing 129 mg linezolid & 112 mg ceftriaxone sodium), or ZnONPs alone (1% w/w). The gel base and medication mixtures were stirred continuously until a homogenous distribution was obtained. A plane gel (unmedicated) was also prepared as a control. The prepared gels were kept in the refrigerator at 4° C. until the next use.

Example 4

Testing In Vivo Antibacterial Efficacy

The in vivo antimicrobial activity of the various gels prepared according to Example 3 was tested in an experimental infection using a rat model. Briefly, 15 albino rats (weighing 120-150 g) were divided into 5 groups (each group contains 3 animals), as described previously (Mekkawy A. I. et al., "In vitro and in vivo evaluation of biologically synthesized silver nanoparticles for topical applications: effect of surface coating and loading into hydrogels", Int. J. Nanomedicine, 12: pp. 759-777 (Jan. 23, 2017)). Rats were anesthetized, skin on the surface was shaved and an incision wounds of 1 $cm^2$ were made using sterile scissors. Then, each wound was infected with bacterial suspension of MRSA ($5 \times 10^6$ CFU). Group I was established as a control and received the unmedicated gel twice daily. Group II received ZnO loaded gels, group III received linezolid alone loaded gels, group IV received ceftriaxone alone loaded gels, and group V received linezolid-ceftriaxone-ZnO loaded gels.

To elucidate the wound-healing-promoting activity of the linezolid-ceftriaxone-ZnO loaded gel preparations, the expression of procollagen type I in skin punch biopsies of the treated rats was evaluated on day 4 using the RT-PCR method as previously described. Analysis was carried out using the primers procollagen type I including: sense primer 5'-AGGACAAGAGGCATGTCTGGTT-3' (SEQ ID NO: 1) and antisense 5'-TTGCAGTGGTAGGTGATGTTCTG-3' (SEQ ID NO: 2). For GAPDH, the primers included the sense primer 5'-TGTTGCCATCAATGACCCCTT-3' (SEQ ID NO: 3) and antisense primer 5'-CTC-CACGACGTACTCAGCG-3' (SEQ ID NO: 4). The experiment was performed using a 7500 Fast Real-Time PCR machine (Applied Biosystems, USA). GAPDH was used to normalize the data. The fold-change in the expression of procollagen was estimated using the $2^{-\Delta\Delta ct}$ method and expressed as relative to the control group.

Figure 1B:
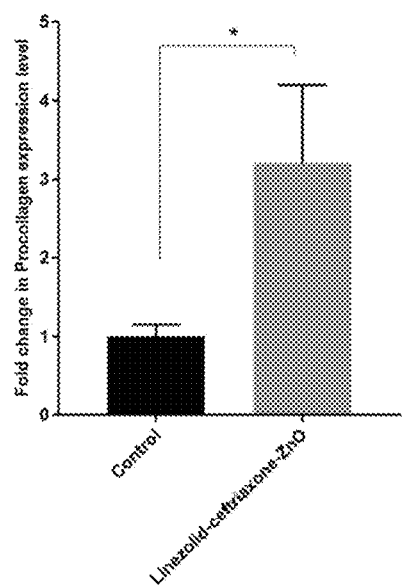
FIG. 1B depicts a graph comparing procollagen I in skin biopsies of rats treated with either the unmedicated control gel or the gel loaded with linezolid-ceftriaxone-ZnO nanoparticles (RT-PCR results are expressed as mean ±SD of 3 replicates, * denotes P value <0.05).

Generally, treated rats showed better wound healing compared to the control group that received unmediated gel. However, the wound healing was markedly improved in group V which received Linezolid-ceftriaxone-ZnO loaded gel (See FIG. 1A). In addition, after 4 days of treatment, the expression of procollagen I was analyzed in skin biopsies of treated rats (See FIG. 1B). Procollagen was expressed at a higher level (3.2±1.1, p=0.02 by unpaired t-test) in the rats treated with Linezolid-ceftriaxone-ZnO loaded gels compared to the control group.

It is to be understood that the combination treatment for antibiotic resistance infections is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making a composition comprising zinc oxide nanoparticles loaded with linezolid and ceftriaxone, comprising:
   (a) mixing an aqueous solution of zinc oxide nanoparticles with an aqueous solution comprising equal weights of ceftriaxone sodium and linezolid to produce a mixture;
   (b) incubating and shaking the mixture;
   (c) filtering the mixture to obtain the zinc oxide nanoparticles loaded with linezolid and ceftriaxone, wherein the method further comprises:
   (a1) heating *Echinacea purpurea* liquid extract to 80° C.;
   (b1) adding zinc nitrate hexahydrate to produce a white precipitate;
   (c1) drying and heating the white precipitate to obtain zinc oxide nanoparticles; and
   (d1) adding the zinc oxide nanoparticles to a solvent to obtain the aqueous solution of zinc oxide nanoparticles.

2. A method of making a gel including a composition comprising zinc oxide nanoparticles loaded with linezolid and ceftriaxone, comprising:
   (a) mixing an aqueous solution of zinc oxide nanoparticles with an aqueous solution comprising equal weights of ceftriaxone sodium and linezolid to produce a mixture;
   (b) incubating and shaking the mixture;
   (c) filtering the mixture to obtain the zinc oxide nanoparticles loaded with linezolid and ceftriaxone;
   (d) dispersing hydroxypropyl methylcellulose (HPMC) polymer distilled water preheated to 80° C. to create a polymer solution;
   (e) stirring the polymer solution; and
   (f) adding the zinc oxide nanoparticles loaded with linezolid and ceftriaxone.

3. The method of claim 2, wherein the aqueous solution of zinc oxide nanoparticles is prepared by:
   (a) heating *Echinacea purpurea* liquid extract to 80° C.;
   (b) adding zinc nitrate hexahydrate to produce a white precipitate;
   (c) drying and heating the white precipitate to obtain zinc oxide nanoparticles; and
   (d) adding the zinc oxide nanoparticles to a solvent to obtain the aqueous solution of zinc oxide nanoparticles.

* * * * *

UNITED STATES PATENT AND TRADEMARK OFFICE
CERTIFICATE OF CORRECTION

| | | |
|---|---|---|
| PATENT NO. | : 12,083,220 B1 | Page 1 of 1 |
| APPLICATION NO. | : 18/512722 | |
| DATED | : September 10, 2024 | |
| INVENTOR(S) | : Hany Mohamed Abd El-Lateef Ahmed et al. | |

It is certified that error appears in the above-identified patent and that said Letters Patent is hereby corrected as shown below:

On the Title Page

Item (72):
Please remove Inventor 3 residence "AL-Ahsa (SA)" and replace with "Assuit (EG)".
Please remove Inventor 4 residence "AL-Ahsa (SA)" and replace with "Sohag (EG)".
Please remove Inventor 5 residence "AL-Ahsa (SA)" and replace with "Sohag (EG)".

Signed and Sealed this
Eighth Day of October, 2024

Katherine Kelly Vidal
*Director of the United States Patent and Trademark Office*

SEQUENCE LISTING

Sequence total quantity: 4
SEQ ID NO: 1          moltype = DNA   length = 22

```
FEATURE                 Location/Qualifiers
source                  1..22
                        mol_type = other DNA
                        organism = Rattus rattus
SEQUENCE: 1
aggacaagag gcatgtctgg tt                                           22

SEQ ID NO: 2            moltype = DNA  length = 23
FEATURE                 Location/Qualifiers
source                  1..23
                        mol_type = other DNA
                        organism = Rattus rattus
SEQUENCE: 2
ttgcagtggt aggtgatgtt ctg                                          23

SEQ ID NO: 3            moltype = DNA  length = 21
FEATURE                 Location/Qualifiers
source                  1..21
                        mol_type = other DNA
                        organism = Rattus rattus
SEQUENCE: 3
tgttgccatc aatgacccct t                                            21

SEQ ID NO: 4            moltype = DNA  length = 19
FEATURE                 Location/Qualifiers
source                  1..19
                        mol_type = other DNA
                        organism = Rattus rattus
SEQUENCE: 4
ctccacgacg tactcagcg                                               19
```